United States Patent
Mui et al.

(10) Patent No.: US 6,379,656 B2
(45) Date of Patent: Apr. 30, 2002

(54) LIQUID COMPOSITION USED FOR DISSOLVING FINGERNAIL POLISHES

(75) Inventors: Ronnie F. Mui, Reading, PA (US); Thomas R. Candia, Cedar Grove, NJ (US); George H. Armstrong, Dayton, NJ (US); Michelle E. Pepe, S. Plainfield, NJ (US)

(73) Assignee: Tevco, Inc., South Plainfield, NJ (US)

( * ) Notice: Subject to any disclaimer, the term of this patent is extended or adjusted under 35 U.S.C. 154(b) by 0 days.

(21) Appl. No.: 09/769,167

(22) Filed: Jan. 25, 2001

Related U.S. Application Data

(63) Continuation-in-part of application No. 09/416,573, filed on Oct. 12, 1999, now Pat. No. 6,187,299.

(51) Int. Cl.$^7$ .............................. A61K 6/00; A61K 7/00; A61K 7/04

(52) U.S. Cl. .......................................... 424/61; 424/401
(58) Field of Search ..................................... 424/61, 401

(56) References Cited

U.S. PATENT DOCUMENTS 6,187,299 B1 * 2/2001 Wimmer et al. .............. 424/61

* cited by examiner

*Primary Examiner*—Thurman K. Page
*Assistant Examiner*—S. Howard

(57) ABSTRACT

A liquid composition used for dissolving fingernail polishes contains three non-miscible liquid phases which, when the composition is left still, are superimposed one on the other. The upper phase is oily. The intermediate phase is the solvent phase and contains solvents immiscible with water. In addition to a tri-phase composition also a bi-phase composition is described. The solvents are a mixture of methyl acetate and tert-butyl acetate.

9 Claims, No Drawings

LIQUID COMPOSITION USED FOR DISSOLVING FINGERNAIL POLISHES

This application is a Continuation-in-part of U.S. Ser. No. 09/416,573 filed Oct. 12, 1999 now U.S. Pat. No. 6,187,299.

FIELD OF THE INVENTION

The present invention relates to nail polish removers and specifically to novel liquid compositions which dissolve fingernail polishes and which are constituted by three or two liquid phases, not miscible, which are superimposed one over the other when the compositions remain still. This invention can be formulated as a "Bi-Phase" or "Tri-Phase" remover. The Bi-Phase contains two separate layers: a solvent phase top layer and an aqueous phase bottom layer. The Tri-phase contains an oil phase top layer, a solvent phase middle layer and an aqueous phase bottom layer. The present invention is designed for the purpose of conditioning and protecting nails and cuticles while removing the nail enamels simultaneously.

In U.S. Ser. No. 09/416,573 the composition comprises three liquid and immiscible phases, the phases being superimposed one on the other when the composition is still. The top phase comprises from 9.8% to 30% by weight of at least an oil a) selected from the group consisting of mineral oils and vegetable oils which are in liquid form at a temperature ranging from 40° F. to 120° F.

The solvent phase comprises from 20% to 56% by weight of at least one removing nail enamel solvent b) which is immiscible with water, and which is other than a hydrocarbon; from 0.1% to 24% by weight of at least one removing nail enamel solvent c) which is miscible with water—the total weight of solvents b) and c) in the composition being from 20.1% to 70% by weight.

The bottom phase comprises from 8 to 40% by weight of water; and from 8% to 35% by weight of at least one glycol polymer d) having an average molecular weight in the range of 200 to 1200. The glycol is selected from the group consisting of polyethylene glycols and polypropylene glycols.

In the examples in U.S. Ser. No. 09/416,573 the solvent immiscible with water is ethyl acetate and the solvent miscible with water is acetone.

It has now been found that substantial improvements are achieved if instead of the ethyl acetate the composition contains about 25–70% of methyl acetate and 0.5–10% of tert-butyl acetate. One advantage recently achieved is the elimination of acetone or solvent which may dehydrate the fingernail and cuticles.

The mixture of these two solvents also permits to obtain a bi-phase, that is a composition comprising only a solvent phase and an aqueous phase. This bi-phase composition is totally new in this Continuation-in-part application.

The tri-phase composition consists of a

| Top Layer: | Oil Phase |
|---|---|
| Middle Layer: | Solvent Phase |
| Bottom Layer: | Aqueous Phase |

As shown in the Table hereinbelow, the total formulation consists of

| MATERIALS | WEIGHT % |
|---|---|
| Mineral Oil | 19.621 |
| Methyl Acetate | 25.868 |
| Tert-Butyl Acetate | 8.74 |
| Deionized Water | 31.00 |
| P425 PPG | 14.634 |
| Benzophenone-1 UV Stabilizer | 0.006 |
| Benzophenone-4 UV Stabilizer | 0.002 |

The composition may also contain coloring materials and a fragrance as shown in the Table hereinbelow.

| D&C Yellow #11 | 0.075% |
|---|---|
| FD&C Green #6 | 0.009 |
| D&C Red #33 | 0.007 |

The composition of the three phases is as shown in the Table hereinbelow.

| Phases | OIL PHASE | SOLVENT PHASE | AQUEOUS PHASE |
|---|---|---|---|
| | Oil(s)[1]: 98.00–100.00% | Solvent(s)[2]: 50.00–80.00% | Water: 40.00–99.998% |
| | | Glycol(s)[3]: 20.00–50.00% | Glycol(s): 0.00–60.00% |
| | Oil soluble dye(s): 0.00–2.00% | Solvent soluble dye(s): 0.00–2.00% | Water & solvent soluble dye(s): 0.00–2.00% |
| | UV stabilizer(s): 0.001–0.01% | UV stabilizer(s): 0.001–0.01% | UV stabilizer(s): 0.001–0.01% |
| | Fragrance(s): 0.001–0.01% | Fragrance(s): 0.001–0.01% | Fragrance(s): 0.001–0.01% |
| | | | Solvent(s)[1]: 0.00–60.00% |
| 2 | | Top layer: 20.00–70.00% | Bottom layer: 20.00–60.00% |
| 3 | Top layer: 10.00–30.00%[3] | Middle layer: 40.00–70.00%[3] | Bottom layer: 20.00–40.00%[3] |

The oil is selected from the group of oil that is in liquid at a temperature from 40° F. to 120° F., including but not limited to mineral oil castor, etc.

The solvents are methyl acetate and tertbutyl acetate.

Glycols are selected from the group of polypropylene glycol and the group of polyethylene glycol

| The formulation for each phase | | | | | |
|---|---|---|---|---|---|
| Top Layer: Oil Phase | | Middle Layer: Solvent Phase | | Bottom Layer: Aqueous Phase | |
| Mineral Oil 70: | 99.60% | Methyl Acetate: | 59.060% | DI Water: | 92.451% |
| D&C Yellow #11 | 0.380% | t-Butyl Acetate: | 7.500% | t-Butyl Acetate: | 7.519% |
| Benzophenone-1 | 0.010% | Benzophenone-1 | 0.010% | Benzophenone-4 | 0.010% |

-continued

The formulation for each phase

| Top Layer: Oil Phase | | Middle Layer: Solvent Phase | | Bottom Layer: Aqueous Phase | |
|---|---|---|---|---|---|
| Lilac Fragrance: | 0.010% | P-425 PPG: | 33.410% | D&C Red #33: | 0.02% |
| | | FD&C Green | 0.020% | | |
| Total | 100.000 | Total | 100.000 | Total | 100.000 |
| | 19.7% | | 43.8% | | 36.5% |

The Bi-Phase composition consists of a

| Top Layer: | Solvent Phase |
|---|---|
| Bottom Layer: | Aqueous Phase |

Coloring materials and a fragrance are preferably added.

| Materials | Weight % |
|---|---|
| Methyl Acetate | 24.930 |
| t-Butyl Acetate | 15.000 |
| P425 PPG | 20.046 |
| FD&C Green #6 | 0.012 |
| Benzophenone-1 | 0.006 |
| Fragrance | 0.006 |
| DI Water | 39.952 |
| D&C Red #33 | 0.008 |
| Preservative | 0.040 |
| Total | 100.000 |

The formulation for each phase

| Top Layer: Solvent Phase | | Bottom Layer Aqueous Phase | |
|---|---|---|---|
| Methyl Acetate | 41.550% | DI Water: | 99.880% |
| t-Butyl Acetate | 25.000% | D&C Red #33 | 0.02% |
| P425 PPG | 33.410% | Preservative | 0.100% |
| FD&C Green #6 | 0.020% | | |
| Benzophenone-1 | 0.010% | | |
| Fragrance | 0.010% | | |
| Total | 100.000 | | 100.000 |
| | 60% | | 40% |

PREPARATION OF THE TOP LAYER: OIL PHASE

At least one oil, for instance a mineral oil, is mixed at low speed with a coloring agent. When the solution is uniform 0.01% Benzophenone-1 as a UV stabilizer is added and then 0.01% of a Lilac Fragrance.

PREPARATION OF THE MIDDLE LAYER: SOLVENT PHASE

Methyl acetate in the amount of 59.060% and tert-butyl acetate in the amount of 7.500% are mixed. The mixer is turned at slow speed. Then polypropylene glycol, P425PPG, in the amount of 20–50%, preferably 23.41% is added. Then FD&C Green #6 0.02% is added. When the solution is uniform, Benzophenone-1 0.01% is added. The mixture is mixed at a slow to medium speed for 15 mins. The total of the preferred amounts is 100%.

PREPARATION OF THE BOTTOM LAYER: AQUEOUS PHASE

In a clean plastic tank deionized water in the amount of preferably 92.451%, is mixed at low speed with coloring agents and Benzophenone-4.

When the composition is left still, it is in the form of three or two liquid phases superimposed one on the other. Simply by agitation, prior to being used, the composition is obtained in the form of an emulsion which is applied on the fingernail polishes. This emulsion permits to eliminate the fingernail polish while in the same time conditioning the nails and cuticles.

What is claimed is:

1. A nail and cuticles composition comprising three liquid and immiscible phases, the phases being superimposed one on the other when the composition is still, the top phase being an oil phase, said oil phase being at least one oil selected from the group consisting of mineral oils and vegetable oils which are in the liquid form at a temperature of 40° F.–120° F., the solvent phase comprises methyl acetate and tert-butyl acetate and the aqueous phase comprises 31% of water.

2. The composition according to claim 1 wherein said oil phase comprises benzophenone-1 which is an ultraviolet radiation stabilizer.

3. The composition according to claim 1 which additionally comprises D & C yellow No. 11, FD & C green No. 6, and D & C Red No. 33.

4. The composition according to claim 1 wherein said solvent phase comprises an ultaviolet radiation stabilizer, a glycol which is a member selected from the group consisting of polypropylene glycols and polyethylene glycols.

5. The composition according to claim 4 wherein said glycol is polypropylene glycol.

6. The composition according to claim 1 wherein said aqueous phase comprises a glycol which is a member selected from the group consisting of polypropylene glycols and polyethylene glycols and benzophenone-4 as an ultraviolet radiation stabilizer.

7. A composition comprising two liquid and immiscible phase, the top layer being the solvent phase and the bottom layer being the aqueous phase, the solvent phase comprising methyl acetate and tert-butyl acetate, benzophenone-1 as a stabilizer, the aqueous phase comprising water and a preservative.

8. The composition according to claim 7 which additionally comprises coloring agents and a fragrance.

9. The composition according to claim 7 wherein said top solvent phase comprises polypropylene glycol and the bottom aqueous layer comprises a preservative.

* * * * *